United States Patent [19]
Cathey et al.

[11] Patent Number: 5,399,486
[45] Date of Patent: Mar. 21, 1995

[54] DISPOSABLE UNIT IN DIAGNOSTIC ASSAYS

[75] Inventors: Cheryl A. Cathey, Palo Alto; Henry L. Schwartz, San Francisco, both of Calif.

[73] Assignee: Biocircuits Corporation, Burlingame, Calif.

[21] Appl. No.: 19,469

[22] Filed: Feb. 18, 1993

[51] Int. Cl.⁶ .................... C12Q 1/00; G01N 33/53; G01N 33/566; G01N 33/543
[52] U.S. Cl. .................... 435/7.9; 435/7.1; 435/7.2; 435/7.92; 435/7.93; 435/7.94; 435/7.95; 436/501; 436/518; 436/519; 436/537; 422/55; 422/58; 422/63
[58] Field of Search ............ 435/7.1, 7.2, 7.92, 435/7.93, 7.94, 7.95; 436/501, 518, 519, 537; 422/55, 58, 63

[56] References Cited

U.S. PATENT DOCUMENTS

| | | | |
|---|---|---|---|
| 5,051,237 | 9/1991 | Grenner et al. | 422/56 |
| 5,053,197 | 10/1991 | Bowen | 422/58 |
| 5,096,836 | 3/1992 | Macho et al. | 436/169 |
| 5,156,810 | 10/1992 | Ribi | 422/82.01 |
| 5,164,598 | 11/1992 | Hillman et al. | 250/341 |

*Primary Examiner*—Esther M. Kepplinger
*Assistant Examiner*—David R. Preston
*Attorney, Agent, or Firm*—Bertram I. Rowland; Bret E. Field

[57] ABSTRACT

A disposable diagnostic unit is provided which employs a housing which provides for a sample port, and a channel which feeds the sample to an incubation area by means of capillary action. The incubation area is underneath an optically-clear window and comprises a lipid membrane which has optical properties, particularly fluorescent properties and usually a reagent. A reservoir at the end of the channel downstream from the incubation area receives the sample and waste washes, while on one side of the platform area is a reagent reservoir and on the other side a side waste reservoir, so that one can move the reagent from the reagent reservoir through the platform area into the waste reservoir. Various reagents may be contained within the unit and the necessary liquids added automatically by appropriate instrumentation, so as to have the assay carried out automatically, without technician involvement, providing an accurate and sensitive determination.

18 Claims, 4 Drawing Sheets

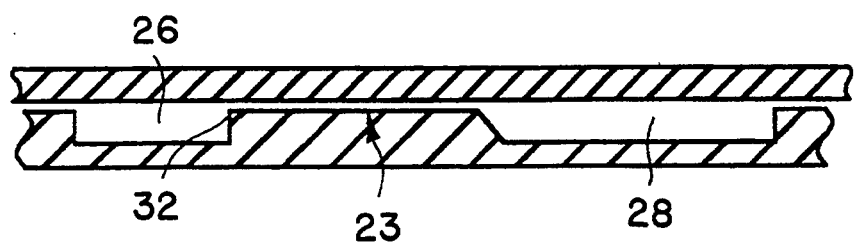
F I G. 2
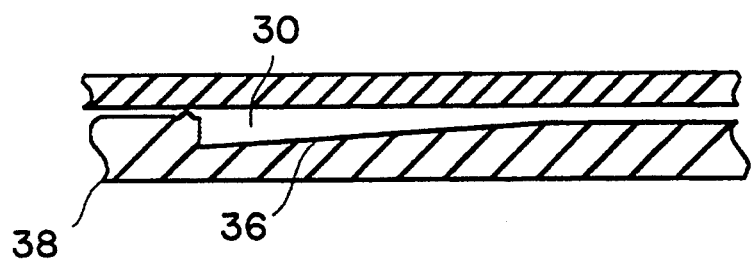
F I G. 3

DISPOSABLE UNIT IN DIAGNOSTIC ASSAYS

TECHNICAL FIELD

The field of this invention is disposable diagnostic units.

BACKGROUND

Despite the numerous strides that have been made in the last two decades in the development of diagnostic reagents and instruments, efforts continue to make diagnoses more accurate, simpler, and more available to non-technical personnel in a wide variety of environments. There is continuing interest in being able to carry out individual assays by non-technical personnel at such sites as doctor's offices, clinics, the home, rest homes, and the like. In order to ensure that non-technical individuals may accurately perform these assays, it is essential that the protocols be simple, there be few if any measurements, and the readings be relatively automatic.

For this purpose, it is desirable to have a disposable unit which can be used individually for each determination. The disposable can provide the various reagents which are necessary for the determination, serve to ensure their mixing, and allow for the proper fitting into a device which provides the final determination. In this manner, one can be relatively assured that assay determinations may be made rapidly and with a minimum opportunity for error in quantitation.

Even in clinical laboratories, there are many opportunities for measuring an analyte in an individual determination. Frequently, particular analytes may be determined only a few times in any one day, so that individual determinations will be the most efficient. Where one can use a disposable unit which only requires the addition of the sample to the disposable unit, great labor savings may be realized, since individuals of high technical qualification would not be required and accuracy would be relatively assured.

There is, therefore, a continuing need for devices employing disposable units, where the units allow for the performance of the assay protocol, with minimal measurement and input from the operator, while allowing for sensitive and accurate quantification of the amount of analyte in a sample.

A long-standing difficulty with disposable units has been efficient washing to remove unbound reagents from the measurement area. The present invention solves this problem by eliminating all side walls, which allows sequential orthogonal washing and leaves no stagnant areas where excess reagent could reside and interfere with the test measurement.

SUMMARY OF THE INVENTION

The subject devices comprise one or more quantitation units. Each unit has a sample application port from which the sample moves to a sample incubation area under an optically-clear window. On one side of the sample incubation area is a side waste reservoir having a vent port having an angled wall rising from the floor of the waste reservoir to the floor of the sample incubation area. The angle is selected to minimize flow of sample into the waste reservoir. At the other side of the sample incubation area is a reagent reservoir with a port for fluid addition, having a vertical wall rising from the floor of the reagent reservoir to the floor of the sample incubation area. The vertical wall minimizes the flow of sample into the reagent reservoir, but allows for flow from the reagent reservoir to the sample incubation area. The final border of the sample incubation area leads to a top waste reservoir.

The assay is carried out by applying the sample to the sample application port, whereby the sample is transported by capillary action to the sample incubation area. In the sample incubation area is a film which binds to analyte or reagent cross-reactive with analyte, the film and reagent being on opposing walls. After incubation of the sample, by adding a liquid to the sample application port, the sample incubation area is washed substantially free of sample. Liquid is then added through the reagent side reservoir port, where a second reagent is dissolved and overflows the sample incubation area with excess flowing into the side waste reservoir and potentially the top waste reservoir. After a predetermined time one or more readings may be made and the amount of analyte determined from the readings.

BRIEF DESCRIPTION OF THE FIGURES

FIG. 2 is a cross-section of the disposable along line 2—2.

FIG. 3 is a cross-section of the disposable along line 3—3.

DESCRIPTION OF THE SPECIFIC EMBODIMENTS

Figure 1:
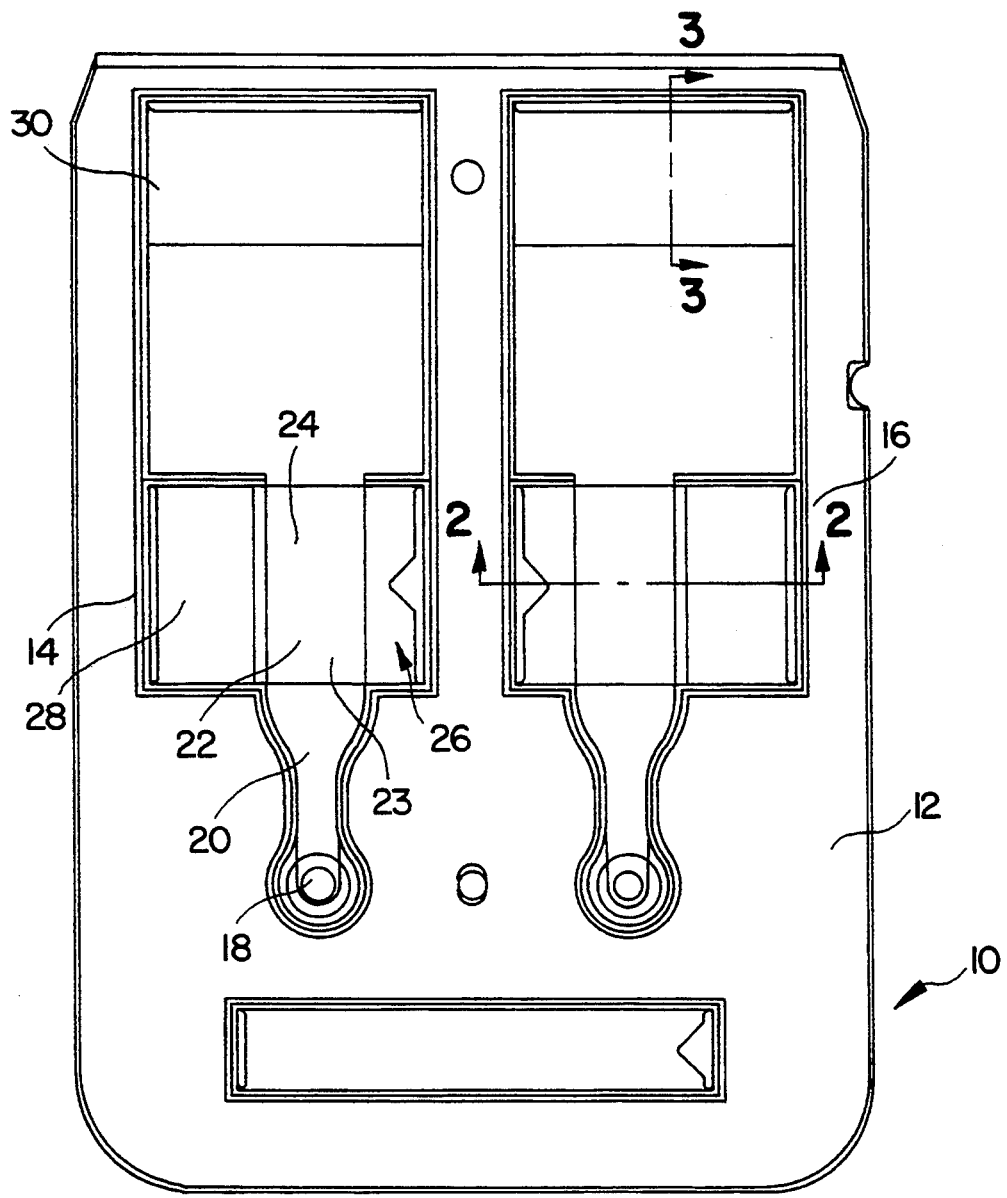
FIG. 1 is a plan view of the disposable.

A disposable unit is provided for optical determination, particularly fluorescent determination, of an analyte. The device provides for a port for sample introduction and a channel which provides for transport of the sample to a sample incubation area. Transport is achieved by capillary action. The sample incubation area has opposing faces: a platform where reagent may be placed, which may be situated lower; and an assay measurement surface below an optically clear window, which may be situated higher than the opposing face forming the channel, during the reading. The platform provides for one or more members of a signal-producing system, which are present on the platform. The platform has in the plane of the platform, on one side, a reagent reservoir and on the other side, a waste reservoir. The remaining side of the platform extends into a top waste reservoir. A port is provided for introduction of liquids into the reagent reservoir. The shape of the various components of the disposable unit are designed to control direction of flow at various stages of the assay. Desirably, the disposable is introduced into an automatic device, which provides for the introduction of one or more fluids into the device in accordance with an appropriate schedule and reads the device to determine the nature and amount of analyte.

The device supports a method which provides for various reagents of a signal-producing system to be present in the device, so as to avoid any measuring of such reagents. One signal-producing system is described in U.S. Pat. No. 5,156,810. This system employs a polymerized lipid layer which is highly fluorescent upon irradiation with light within an appropriate wavelength range. Proximal to one face of the layer is a member of a specific binding pair, where the pair consists of ligand and receptor. The lipid layer is applied to assay the measurement surface. Various techniques may be employed for applying a lipid layer to the assay measurement surface. On the opposite side of the channel of the incubation area is a labeled reagent which comprises a member of a specific binding pair. This labeled reagent pair member is cross-reactive with, i.e., competitive or complementary to, i.e. capable of binding to, the pair member of the lipid layer. The reagent specific binding pair member is conjugated to a label which provides for a detectable signal in conjunction with the lipid layer. Where the signal from the lipid layer is an optical signal, the labeled conjugate will directly or indirectly modulate the optical signal in relation to the amount of analyte which is in the sample or specimen.

In a preferred embodiment, the label will be an enzyme which acts on a substrate to produce a product which can interact with the membrane layer. The product may be a fluorescer, a quencher, a dye which absorbs light in the wavelength range of irradiation, or other compound which may serve to modulate the observed optical signal in relation to the amount of analyte in the sample.

Alternatively, one may use labels other than an enzyme. The choice of other label will depend upon the sensitivity desired, the manner of detection, the nature of the sample, as well as the analyte, and the like. Thus, one may use fluorescent labels, which can provide for channeling of the energy from the membrane label to the fluorescer, so as to provide a substantial Stokes shift, whereby the emitted light is substantially displaced from the light absorbed by the membrane and light which would otherwise be emitted from the membrane. One may also use fluorescers which have significant delay times, such as chelated lathanides, so that upon irradiation, one delays the reading to allow for other fluorescence to die down.

Where an enzyme is the label, the reagent reservoir to the side and adjacent to the platform will contain substrate for the enzyme. Thus, at an appropriate time, one can introduce substrate from the reagent reservoir to the incubation area in an orthogonal manner to the direction of flow of the sample, so as to wash the platform, as well as provide substrate. Downstream from the platform will be a large waste reservoir which will serve to receive the sample and washing solutions which are introduced into the sample port and flow through the channel to the platform and exit into the top waste reservoir.

In carrying out an assay, one may employ any type of liquid sample, which frequently may be used directly or may be subjected to prior treatment, depending upon the nature of the sample and the analyte. The sample may be from any source, such as a physiological source, such as blood, serum, plasma, urine, saliva, spinal fluid, lysate, etc.; sample of ecological interest, such as water, soil, waste streams, organisms, etc.; food, such as meat, dairy products, plant products, etc.; drugs or drug contaminants in processing; or the like. The analyte may be any type of compound, such as small organic molecules, peptides and proteins, sugars, nucleic acids, lipids and combinations thereof, naturally occurring or synthetic or combinations thereof, so long as there is a complementary binding member.

The analyte may be any compound which can be detected and is a member of a specific binding pair, either ligand or receptor. The term "receptor" is used arbitrarily, since its origin had to do with surface membrane proteins, where the compound which bound to the surface membrane protein was referred to as a ligand. Receptors include naturally occurring receptors, e.g. enzymes, lectins, surface membrane proteins, antibodies, recombinant proteins, etc., synthetic receptors, nucleic acids, etc. For the purpose of the subject invention, it is sufficient that two molecules have a significant affinity for each other, where the binding constant will usually be at least about $10^7$ mol$^{-1}$ and one may choose to refer to either member as the receptor. Compounds of interest have to some degree been indicated by indicating the various sample sources. The analytes will frequently include drugs, both naturally-occurring and synthetic, various components of animals, including humans, such as blood components, tissue components, and the like; microorganisms, such as bacteria, fungi, protista, viruses, and the like; components of waste streams or products or contaminants of such products in commercial processing; components in the environment, particularly contaminants, such as pesticides, microorganisms, and the like.

Depending upon the nature of the sample, the sample may be subjected to prior treatment, such as extraction, distillation, chromatography, gel electrophoresis, dialysis, dissolution, centrifugation, filtration, cell separation, and the like. For blood, one may wish to remove red blood cells to provide plasma or serum but their removal is not necessary. Various media may be employed, which will allow for providing for a sample solution or dispersion which can be used in the subject unit.

After appropriate treatment, if any, the sample is then introduced into the sample port. The unit may be designed to accept a broad range of volumes as the sample. Thus, the volume of sample may range from about 1 $\mu$l to about 0.5 ml, more usually from about 10 $\mu$l to 250 $\mu$l, preferably from about 25 $\mu$l to 100 $\mu$l. The sample is drawn from the sample application port by capillary action through a sample transport channel. The sample transport channel has upper and lower walls which are sufficiently close, so as to transport the sample by capillary action from the sample port to the incubation area. Similarly, the space between the opposing walls of the incubation area is sufficiently small to continue to move the sample through the incubation area to the top waste reservoir. Thus the sample transport channel and incubation area form a main channel for transport of the sample from the sample port to the top waste reservoir.

The sample is constrained to remain on the platform and not enter the wells adjacent opposite sides of the platform. The wall of one reservoir drops away from the platform at an angle of 90° whereas the other reservoir drops away at the more shallow angle of about 50°. With the increasing space between opposing walls as a result of the dropoff between each of these walls, the decrease in capillary force constrains the sample to remain in the main channel directed toward the top waste reservoir, which maintains the depth of the channel in the incubation area. The sample then continues past the incubation area to the top waste reservoir.

The transport channel may serve a plurality of purposes besides serving as the conduit for movement of the sample. Various reagents may be present in the channel, either diffusibly or non-diffusibly bound to the walls. For example, antibodies may be bound to the walls which would serve to remove one or more components of the sample, e.g. cell, interfering components, etc. Chemical reagents may be present to change the pH, redox potential or other characteristic of the sample. In this way the sample which is introduced into the incubation area may be different from the sample introduced at the sample pad.

The rate of movement of the sample through the incubation area based on capillary forces and the size of the incubation area will be sufficient for substantially all of the analyte to react.

As the sample traverses the platform, the labeled conjugate will be dissolved by the sample and reaction will occur between complementary members. The assay protocol may involve competition or cooperation. In the case of competition, the conjugate will bind to either the analyte or binding sites on the membrane surface. By having a limited number of conjugate molecules, the number of conjugate molecules which can bind to the membrane will be inversely proportional to the number of molecules of analyte in the sample. Thus, the number of labels which become bound to the surface will be inversely proportional to the number of analyte molecules in the sample. This approach will normally be employed with small analytes, particularly haptenic analytes, where the analyte can only bind to a single receptor.

By contrast, with larger analytes, which are polyepitopic, one has the opportunity for two receptors to bind simultaneously or where one is interested in a receptor, the receptor must have at least two binding sites, which binding sites may be the same or different in the cooperative protocol. In this way, the analyte may serve as a bridge between the complementary binding member bound to the membrane and the complementary binding member which is labeled. One may also use the competitive protocol, by having the specific binding pair member of the conjugate capable of competing with the analyte for binding to the membrane. After sufficient time to ensure that substantially complete binding has occurred, the next step may be performed.

After sufficient time for substantially complete reaction of the analyte in the incubation area, so that the member of the specific binding pair present in the sample, the analyte, can bind to the complementary member of the membrane or reagent, the incubation area, particularly the lipid membrane, may then be washed. A buffered aqueous solution may be used which is appropriate for maintaining the binding of the specific binding pair members. Usually, the volume of the wash solution will be at least about equal to the volume of the sample and may be 10-fold more or greater, usually not more than about 7-fold more or greater, and preferably at least about 2-fold greater. One or more washes may be employed by applying the appropriate volume to the sample port. For the reasons given previously, the wash solutions will be directed through the channel past the platform to the top waste reservoir. It is noted that the regions along the edges of the platform may not be completely washed, the regions being relatively static, so that some of the sample medium and components of the sample medium may be retained at these edges.

Where an enzyme is the label, it is necessary to provide substrate for the enzyme to act on, so as to modulate the signal provided by the membrane. The reagent reservoir to one side of the channel, is then flooded, so as to dissolve the substrate and drive the liquid into the incubation area and to some degree into the top waste reservoir. There will be resistance to flow into the top waste reservoir at this time, due to the need to displace the fluid already present in that reservoir, which has resulted in substantially complete filling of the reservoir during the previous wash. In addition, the depth of the top reservoir desirably increases slightly at the far end away from the incubation area. This increase increases the capacity of the top waste reservoir. However, when the fluid fills to that point, the driving force decreases with the increasing depth, so as to reduce the capillary force driving the liquid into this area. The added resistance to flow towards the top reservoir and the decrease in capillary driving force in the direction of the top reservoir offset the decrease in the capillary driving force of flow into the side reservoir, and the fluid begins to flow over the 50° slope into the side reservoir. This lateral flow washes out any residual sample that was at the edges of the incubation area and fills the incubation area with substrate. The enzyme present in the incubation area bound to the lipid membrane may then react with the substrate to provide for the appropriate signal. In the case of a fluorescent measurement, the product could be a quencher which reduces the fluorescence in proportion to the amount of enzyme present and the line of the reading(s).

The housing provides for an optically-clear surface above the platform area, which permits irradiation of the assay measurement surface without attenuation by the sample, so as to excite the membrane. The amount of fluorescent light which is emitted from the platform area is collected and counted and, if desired, compared to a control value with a known amount of analyte, including no analyte. This value may then be related to the amount of analyte in the sample. A single timed measurement or a plurality of measurements to determine a rate may be made.

The various applications of the fluid to the disposable may be carried out manually or automatically, with an appropriate instrument. Thus, the instrument may measure the sample and wash volumes introduced into the unit, time the incubations, maintain constant temperature, and take the reading, as appropriate. With the enzyme reaction, usually the reading will be timed, or two or more readings will be taken at a predetermined interval.

The membrane on the assay measurement surface may be divided up into a plurality of sections, where each section may have the same or different specific binding pair member. In this way, the sample may be assayed simultaneously for a number of different analytes. Depending upon the nature of the different analytes, the same or different conjugates would be present in the incubation area. The assay could be carried out in the same way, except at the time of reading, one would specifically address different regions of the membrane to identify the fluorescence coming from each of the individual regions.

The device which is employed can be varied as to size, usually being at least about 1 cm×3 cm and not more than about 4 cm×8 cm, preferably having the smaller dimension in the range of about 1–3 cm and in the longer direction by about 3–8 cm. While for the most part, the device may be any convenient shape, conveniently, it will be rectangular where the edges may be modified by rounding, cutting the corner(s), or other modification which will allow for easy handling and adapting the device to a reader. The thickness will generally vary from about 1–5 mm, more usually about 1.5–3 mm, where the housing will usually be made of two plates, which will be sealed together. Conveniently, one plate will serve primarily as a cover and provide the ports and optical window(s), while the other plate will provide the various structures necessary for the reservoirs and channels associated with the unit. Therefore, the plate into which the various reservoirs and channel are molded will usually be thicker than the cover plate, generally about 1.5–2-fold thicker than the cover plate. The volume capacity for the various reservoirs may vary widely, the top waste reservoir having a capacity of about 30 μl to 2 mls, while the side waste reservoir will have a volume in the range of about 10 μl to 1 ml. The reagent well will generally have a volume of about 10 μl to 500 μl.

The plates may be molded out of various plastics which allow for reasonably accurate tolerances, can withstand the various chemicals involved, and will allow for the presence of an optically-clear area. Plastics which fulfill these requirements include acrylate, polystyrene, polycarbonate, SAN, ABS, etc.

For further understanding of the invention, the drawings will now be considered.

In FIG. 1, the unit 10 has a housing 12. The unit is shown with first and second assay members 14 and 16. It will be understood that each of the members are the same, except are shown as mirror images. Therefore, only the left-hand member 14 will be discussed. The assay member has a port which connects with channel 20. The channel 20 transports the sample or other fluids introduced into the sample port 18 to the incubation area 22.

The incubation area 22 provides for a number of functions. It is the site where the chemistry occurs, where one has the optically-responsive layer on the upper surface 24. Opposite to the upper surface is the reagent platform 23, which is spaced apart from the upper surface 22. Coated on the surface of the reagent platform 23 is a reagent which serves to react with or compete with the analyte, so that the amount of reagent that becomes bound to the membrane will be related to the amount of analyte in the sample. The spacing in the transport channel 20 will generally be about from about 0.001" to 0.100", usually from about 0.002" to 0.020". Similarly, the spacing in the incubation area will be about 0.002" to 0.040", generally from about 0.005" to 0.015". Where a substrate is necessary, the substrate will be stored in reagent reservoir 26. On the opposite side of platform 22 will be side waste reservoir 28. Therefore, a main channel begins at port 18 and extends through transport channel 20 and incubation area 22 and terminates in top waste reservoir 30.

FIG. 2 is a cross-section along line 2—2 in FIG. 1. The reagent reservoir 26, which seems to store soluble reagent, has wall 32 which is at a steep angle, conveniently a 90° angle in relation to platform 23 and the bottom of reagent reservoir 26. By contrast, the wall between platform 23 and side waste reservoir 28 will be at a more shallow angle, conveniently at about 50° to the floor of waste reservoir 28.

As the depth of the capillary flow channel increases, the capillary force that drives the flow decreases. With a 50° slope, the depth of the capillary increases very quickly over a short distance, thus decreasing the capillary force quite drastically over the same short distance. With a 90° slope, the depth of the capillary changes instantaneously, thus causing a discontinuity in the capillary force which effectively stops the flow over that edge. Thus, the flow of fluid is constrained on either side of the platform by a sharp decrease in capillary force. However, the depth of the capillary channel does not change in the forward direction (toward the top waste reservoir), so the capillary driving force in that direction remains constant. Thus the flow of the sample is unconstrained in the forward direction, and ceases only when the entire sample has passed through the sample application port.

When a buffered wash solution is introduced through the sample port, the buffer displaces the sample and the sample and buffer flow into the top waste reservoir. Again, the flow is constrained on both sides of the platform due to a drop in the capillary force, but is unconstrained in the forward direction. The addition of buffer in the sample application port washes most of the sample into the top reservoir. However, the fluid at the sides of the incubation area is fairly stagnant, thus some sample is left in these regions that does not flow into the top waste reservoir.

When buffer is added to the reagent reservoir, the reagent is rehydrated and flows over the platform area and forces fluid into both the top and side waste reservoirs. The fluid flows over the 50° angle into the side reservoir at this point, but not earlier during the sample addition step, because there is now added resistance to flow into the top reservoir due to the fact that this reservoir is either full or nearly so. This increase in resistance to flow into the top reservoir is due in part to additional energy being necessary to displace the fluid already present in the top reservoir. In addition, as will be discussed, the depth of the top reservoir increases slightly at the far end away from the sample application port, so when the fluid fills to that point, the capillary driving force decreases with the increasing depth. This is shown in FIG. 3, which is a cross-sectional view along line 3—3 in FIG. 1. The floor 36 of top waste reservoir 30 angles at a slight angle downwardly to the back wall 38 of top waste reservoir 30. Conveniently, an angle of about 3.7° serves to provide the reduction in capillary force.

As the top reservoir fills, both the added resistance to flow towards the top reservoir and the decrease in capillary driving force begin to offset the decrease in the capillary driving force of flow into the side reservoir 28, and the fluid begins to flow over the 50° slope into the side reservoir. This lateral flow washes out any residual sample that was at the edges of the platform 23 (and thus previously stagnant) and fills the incubation area 22 with substrate. The reaction then occurs in the incubation area 22 and can be read by an instrument, as appropriate.

Figure 4:
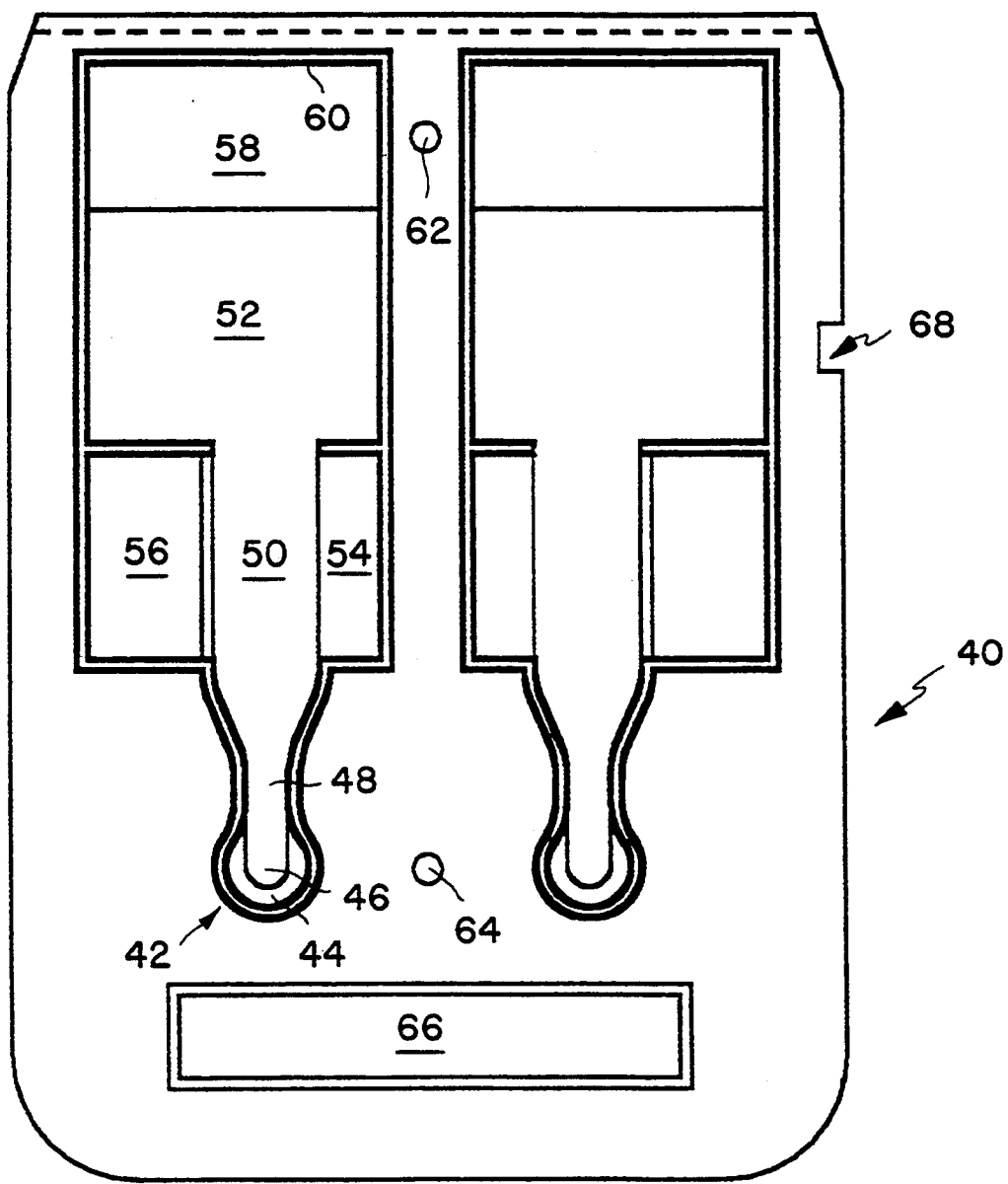
FIG. 4 is a plan view of the bottom housing of the disposable according to FIG. 1.

In FIG. 4 is shown a plan view of the bottom housing 40. The port area 42 has ledge 44 and depression 46 which depression is at the same level as channel 48. The channel maintains a constant depth through the platform reaction area 50 until emptying into top waste reservoir 52. The channel 48 will generally be depressed from the surface of the bottom housing 40. One side of the platform area 50 is the reagent reservoir 54, while on the other side is the side waste reservoir 56. As discussed above, the top waste reservoir gradually descends further from the plane of the top surface of the bottom housing 40 in the region 58 approaching the end wall 60 of the top waste reservoir 52. First and second detents 62 and 64 are provided for registry of the bottom housing with a top housing. A trough 66 is provided which serves to collect priming liquid from the instrument, for instantly filling the conduit feeding liquid to the unit in the instrument. In this way, the instrument need not have an internal reservoir, since each unit will carry away the waste liquid. The back of the trough 66 has ridges, not shown, which serve to make the cartridge easier to hold. A notch 68 serves to register the device in an instrument for reading the results, where a spring-loaded ball bearing may lock the unit in place.

Figure 5:
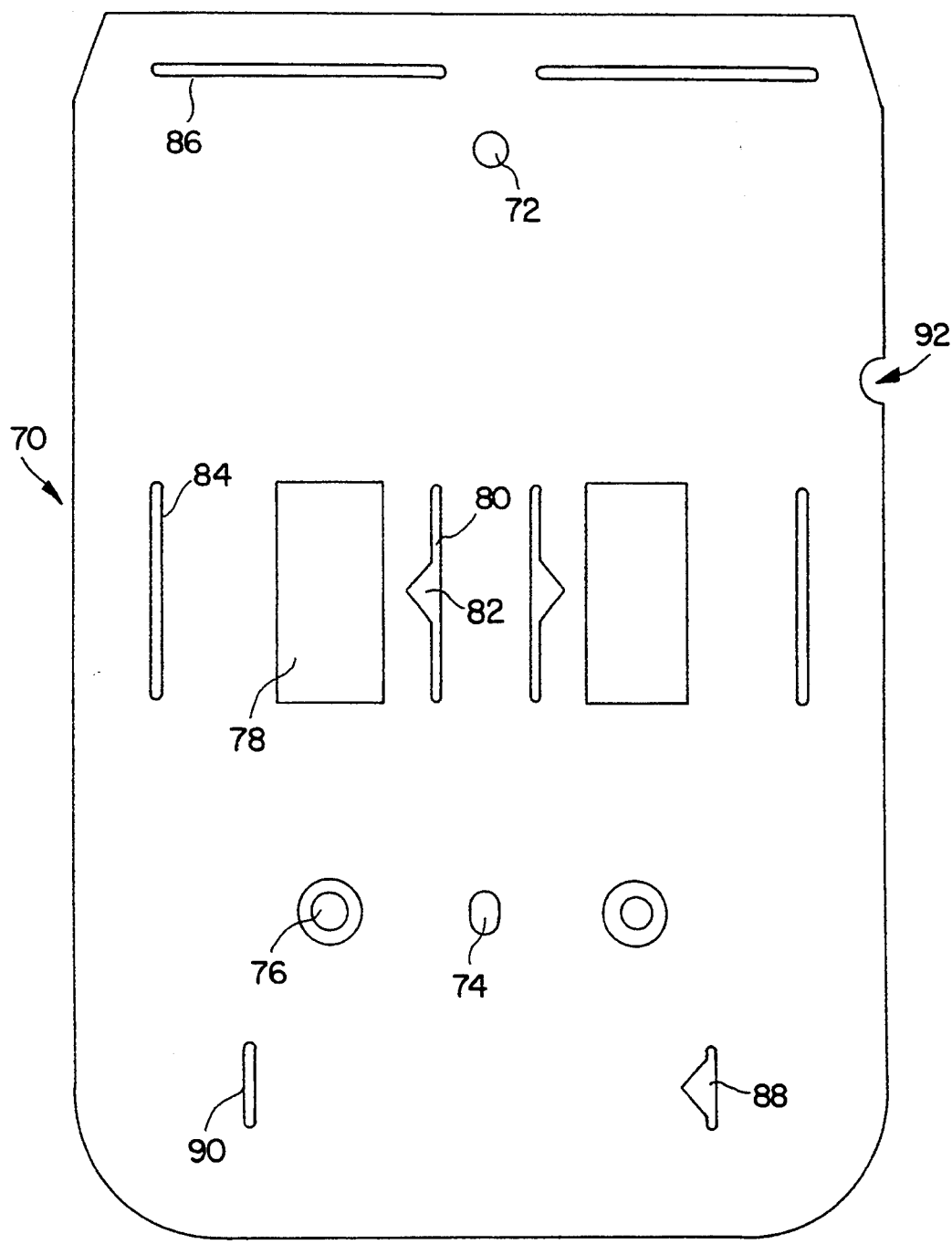
FIG. 5 is a plan view of a top housing of the disposable depicted in FIG. 1.

In FIG. 5 is depicted the top housing or plate 70 having first and second apertures 72 and 74 for receiving detents 62 and 64 as shown in FIG. 4, respectively. Since the two assay members in the housing are the same, as described previously, only the components of one of the assay members will be described.

A sample port 76 is provided to be in register over the port area 42 and depression 46 as shown in FIG. 4. The sample port 76 forms a inverted truncated cone, so as to be able to hold the liquid sample as it feeds the liquid into the channel. Optically clear window 78 is in position directly above incubation area 50 as shown in FIG. 4, while on one side and above the reagent reservoir 54 as shown in FIG. 4 is addition port 82 which is shaped like a slot having a triangular opening to fit with means for adding buffer solution. An air port or vent 84 is provided to allow for the escape of air as liquid passes from the reagent reservoir 54 as shown in FIG. 4 over the platform area 50 to the side waste reservoir 56 as shown in FIG. 4. The use of slots as port vents serves to ensure smooth, uniform spreading of the fluids. A second air port 86 is provided for escape of air from the top waste reservoir 52 as shown in FIG. 4. A notched port 88 provides access to trough 66 as shown in FIG. 4, which also has an air port 90. A notch 92, which has a different conformation from the notch 68 as shown in FIG. 4 of the bottom housing, is in registry with notch 68 and provides space for a ball bearing to lock the unit into place.

The optical window 78 has a lower surface which is in the same plane as the lower surface of the top housing, while being depressed from the plane of the upper surface of the top housing in order to keep the window from being damaged or scratched during the welding process. Desirably, except for the windows 78, the outer surfaces of the bottom and top housings are textured, so as to be translucent.

To assemble the device, the appropriate reagents are placed at their proper sites. The membrane is placed in the incubation upper surface area, substrate, as appropriate, in the reagent reservoir and conjugate is placed on the platform immediately beneath the window. The membrane is readily transferred to the top housing surface under the window by conventional means. After the reagents have been positioned, the top housing can be placed in registry over the bottom housing and the edges sealed by any appropriate means, such as ultrasonic welding, adhesives, etc. The unit is then ready to be stored for subsequent use. Since two assays can be run, the two assay members can be used for a single assay and a control, for the same assay for two samples, or two different assays for the same or different samples. Thus, various configurations of protocols may be employed depending upon the nature of the desired assays. In addition, one may have a unit with a single assay or a plurality of assays greater than two and one can vary the size appropriately, in accordance with the number of assays involved.

It is evident from the above description, that a convenient diagnostic unit is provided, where one can provide for automatic addition of samples and washes, so that assays may be carried out almost completely automatically. Thus, the technical requirements of the operation are quite minimal for operation and one can obtain reproducibility and accuracy with very high sensitivity. The units are easily stored, being flat and thin, so that large packages of units can be readily transported. The reagents are protected from contamination particularly where the unit can be wrapped, so as to insure the substantial absence of moisture and air getting into the unit.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A diagnostic disposable device comprising:
   a housing;
   said housing containing as assay system comprising:
   within said housing, a fluorescent lipid membrane;
   an incubation area in said housing, having opposing walls; a first fall supporting said fluorescent lipid membrane; a second wall supporting a reagent, said walls being spaced apart to provide for capillary flow through said incubation area, wherein said reagent specifically binds to a specific binding pair member proximal to one face of said fluorescent lipid membrane;
   proximal to one end of said housing, a sample port;
   a capillary channel connecting said incubation area to said sample port;
   side reservoirs on each side of said incubation area, said side reservoirs being a reagent storage reservoir and a waste reservoir, and a main waste receiving reservoir downstream from said incubation area opposite from said channel, said main waste and side reservoirs having gas release ports, side reagent storage reservoir having an inlet port; and
   an optically clear window over said fluorescent lipid membrane.

2. A diagnostic disposable device according to claim 1, wherein the side walls of said side reservoirs extending from said second wall drop steeply down to substantially reduce capillary force.

3. A diagnostic disposable device according to claim 1, wherein said housing has a trough, an inlet port and a gas release port for said trough, unconnected with said assay system, wherein said trough serves for receiving priming or other waste fluid and is in a fluid collecting and filling relationship with said assay system.

4. A diagnostic disposable device according to claim 1, wherein the depth of said main waste reservoir increases distal from said incubation area.

5. A diagnostic disposable device comprising:
   a housing;
   said housing comprising a top plate and a bottom plate fastened together, one plate having detents and the other plate having orifices for indexing said plates;
   said housing containing an assay system comprising:
   within said housing, a fluorescent lipid membrane;

an incubation area in said housing, having opposing walls; a first wall supporting said fluorescent lipid membrane; a second wall supporting a reagent, said walls being spaced apart to provide for capillary flow through said incubation area, wherein said reagent specifically binds to a specific binding pair member proximal to one face of said fluorescent lipid membrane:

proximal to one end of said housing, a sample port;

a capillary channel connecting said incubation area to said sample port;

reservoirs on each side of said incubation area, said side reservoirs being a reagent storage reservoir and a waste reservoir, and a main waste receiving reservoir downstream from said incubation area opposite from said channel, said main waste and side waste reservoirs having gas release ports, said side reagent storage reservoir having an inlet port, said gas release port being slots extending along one side of said reservoirs, wherein the side walls of said side reservoirs extending from said second wall drop steeply down to substantially reduce capillary force; and an optically clear window over said fluorescent lipid membrane.

6. A diagnostic disposable device according to claim 5, wherein the side wall of said reagent storage reservoir is at an angle of about 90° and said side wall of said side waste reservoir is at an angle of about 50°.

7. A diagnostic disposable device according to claim 5, wherein said reagent is an enzyme conjugate and said side reagent storage reservoir contains enzyme substrate.

8. A diagnostic disposable device according to claim 5, wherein said housing comprises a plurality of assay systems.

9. A diagnostic disposable device according to claim 5, wherein said housing has a trough, an inlet port and a gas release port for said trough, unconnected with said assay system, wherein said trough serves for receiving priming or other waste fluid and is in a fluid collecting and filling relationship with said assay system.

10. A diagnostic disposable device according to claim 5, wherein the depth of said main waste reservoir increases distal from said incubation area.

11. A diagnostic disposable device according to claim 5, wherein said plates are made of a moldable plastic and said plates are welded together.

12. A method for determining an analyte in a sample comprising:

providing a disposable diagnostic device comprising:
a housing;
said housing containing an assay system comprising:
an incubation area in said housing, having opposing walls; a first wall supporting a fluorescent lipid membrane having a first member of a specific binding pair of Which said analyte is a member proximal to an exposed surface of said membrane and a second wall supporting an enzyme conjugate reagent capable of binding to said first member in proportion to the amount of analyte in said sample, said walls being spaced apart to provide for capillary flow through said incubation area;
proximal to one end of said housing a sample port;
a capillary channel connecting said incubation area to said sample port;
reservoirs on each side of said incubation area, said side reservoirs being a reagent storage reservoir for storing enzyme substrate and a waste reservoir, and a main waste receiving reservoir downstream from said incubation area opposite from said channel, said main waste and side waste reservoirs having gas release ports, side reagent storage reservoir having an inlet port; and
an optically clear window over said fluorescent lipid membrane;

adding sample to the sample port of said diagnostic device, whereby said sample is transported through the capillary channel into said incubation area;

allowing said sample to move through said incubation area into a main waste reservoir downstream from said incubation area, whereby said enzyme conjugate is dissolved and specifically binds to the first members on said fluorescent lipid membrane in proportion to the amount of analyte present in said sample;

introducing wash solution into said sample port, whereby said wash solution washes said incubation area substantially free of sample components and unbound enzyme conjugate;

introducing a buffer solution into a side reagent storage reservoir to dissolve said enzyme substrate and transport said enzyme substrate through said incubation area into the side waste reservoir, whereby enzyme product is produced Which modulates the fluorescence of said fluorescent lipid membrane;

irradiating said fluorescent lipid membrane through said optically clear window, whereby said lipid membrane is excited and fluoresces; and measuring the fluorescence intensity at at least one time to determine the presence of analyte in said sample.

13. A method according to claim 12, wherein said analyte is a hapten.

14. A method according to claim 12, wherein said analyte is an antigen.

15. A method according to claim 12, wherein said analyte and said enzyme conjugate are competitive in binding to the first member on said fluorescent lipid layer.

16. A method according to claim 12, wherein said analyte specifically binds both the first members on said fluorescent lipid membrane and said enzyme conjugate.

17. A diagnostic disposable device comprising:
a housing for use in an assay for determining an analyte;
said housing containing a plurality of areas for providing different functions associated with said assay;
an incubation area having spaced apart walls to provide for capillary flow through said incubation area;
proximal to one end of said housing, a sample port;
a capillary channel connecting said incubation area to said sample port;
side reservoirs on each side of said incubation area, said side reservoirs being a reagent storage reservoir and a waste reservoir, and a main waste receiving reservoir downstream from said incubation area opposite from said channel, said main waste and side waste reservoirs having gas release ports, with said reagent storage reservoir having an inlet port to allow for flow of liquid orthogonal to the direction defined by said capillary channel;
an optically clear window over said incubation area.

18. A diagnostic disposable device according to claim 17, wherein said ports are slot-shaped.

* * * * *